(12) United States Patent
Freitag et al.

(10) Patent No.: US 8,631,797 B2
(45) Date of Patent: *Jan. 21, 2014

(54) SYSTEMS, METHODS AND APPARATUS FOR RESPIRATORY SUPPORT OF A PATIENT

(75) Inventors: Lutz Freitag, Hemer (DE); Gregory Kapust, San Ramon, CA (US); Anthony D. Wondka, Thousand Oaks, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1041 days.

This patent is subject to a terminal disclaimer.

(21) Appl. No.: 12/423,397

(22) Filed: Apr. 14, 2009

(65) Prior Publication Data

US 2009/0255533 A1 Oct. 15, 2009

Related U.S. Application Data

(63) Continuation of application No. 11/523,519, filed on Sep. 20, 2006, now Pat. No. 7,533,670.

(60) Provisional application No. 60/718,318, filed on Sep. 20, 2005.

(51) Int. Cl.
*A61M 16/04* (2006.01)
*A61M 16/00* (2006.01)

(52) U.S. Cl.
USPC ............ 128/207.16; 128/207.14; 128/200.26; 128/204.18; 128/204.23; 128/204.26

(58) Field of Classification Search
USPC ................... 604/164.01–164.13; 128/200.26, 128/204.18, 204.25, 207.14, 207.18, 128/200.24, 205.19, 206.11, 207.29
See application file for complete search history.

(56) References Cited

U.S. PATENT DOCUMENTS

| | | | | |
|---|---|---|---|---|
| 3,610,247 A | * | 10/1971 | Jackson | 128/207.15 |
| 3,794,026 A | * | 2/1974 | Jacobs | 128/200.13 |
| 4,265,237 A | * | 5/1981 | Schwanbom et al. | 128/204.24 |
| 5,181,509 A | | 1/1993 | Spofford et al. | |
| 5,279,288 A | | 1/1994 | Christopher et al. | |
| 6,360,740 B1 | * | 3/2002 | Ward et al. | 128/200.24 |
| 6,390,091 B1 | * | 5/2002 | Banner et al. | 128/204.21 |
| 6,530,370 B1 | * | 3/2003 | Heinonen | 128/200.16 |
| 7,478,634 B2 | * | 1/2009 | Jam | 128/200.24 |
| 7,487,778 B2 | * | 2/2009 | Freitag | 128/207.14 |
| 7,533,670 B1 | * | 5/2009 | Freitag et al. | 128/204.23 |

* cited by examiner

*Primary Examiner* — Annette Dixon
(74) *Attorney, Agent, or Firm* — Stetina Brunda Garred & Brucker

(57) ABSTRACT

Spontaneous respiration is detected by sensors. An additional amount of oxygen is administered to the lungs via a jet gas current at the end of an inhalation procedure. Breathing volume, absorption of oxygen during inhalation, and clearance of carbon dioxide during exhalation are improved. If required, the exhalation procedure of the patient can be arrested or slowed by a countercurrent to avoid a collapse of the respiration paths. An apparatus including an oxygen pump can be connected to an oxygen source and includes a tracheal prosthesis that can be connected via a catheter. The respiration detections sensors are connected to a control unit for activating the oxygen pump. The tracheal prosthesis includes a tubular support body with a connection for the catheter, and the sensors are associated with the support body. The tracheal prosthesis and jet catheter are dimensioned so the patient can freely breathe and speak without restriction.

54 Claims, 14 Drawing Sheets

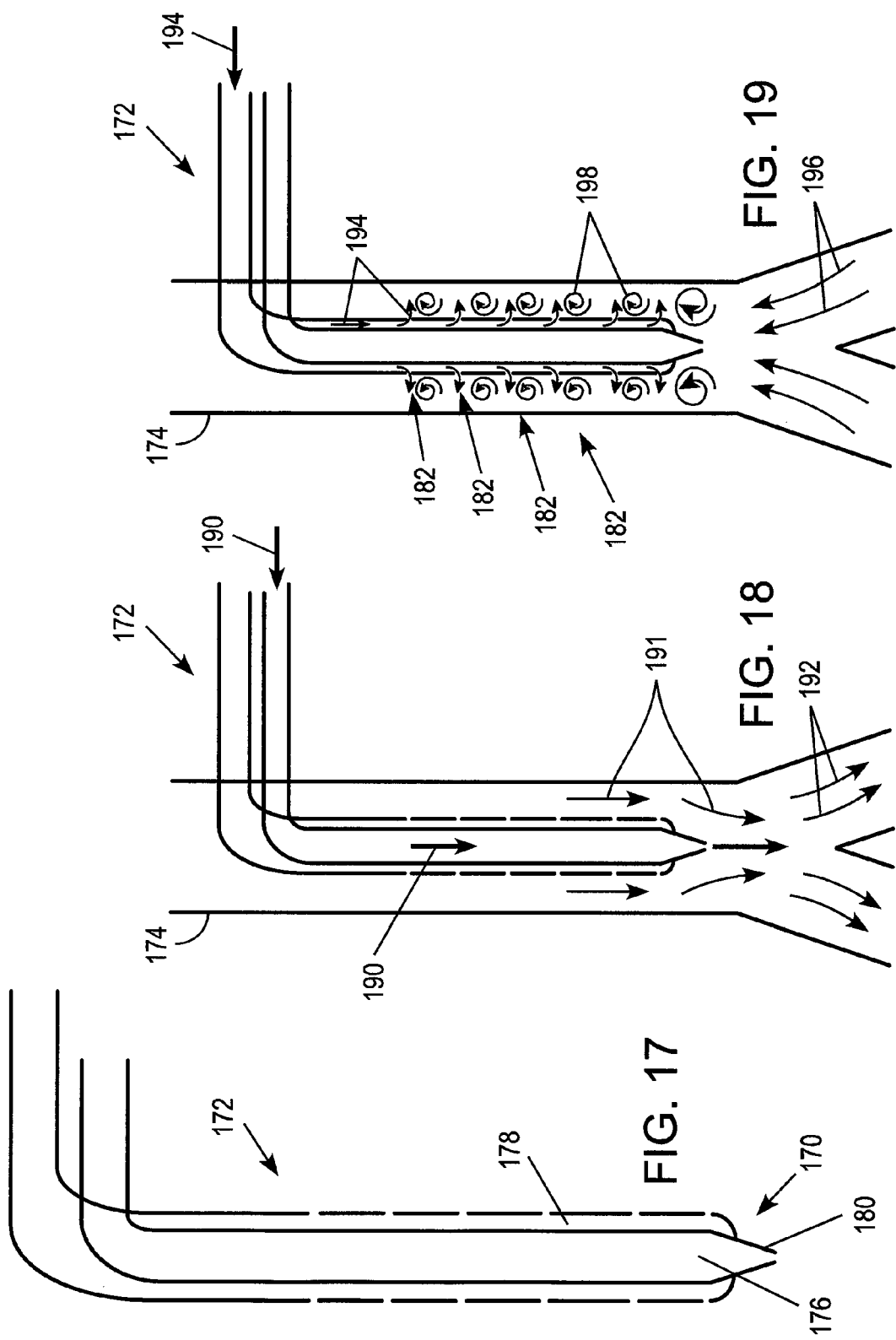

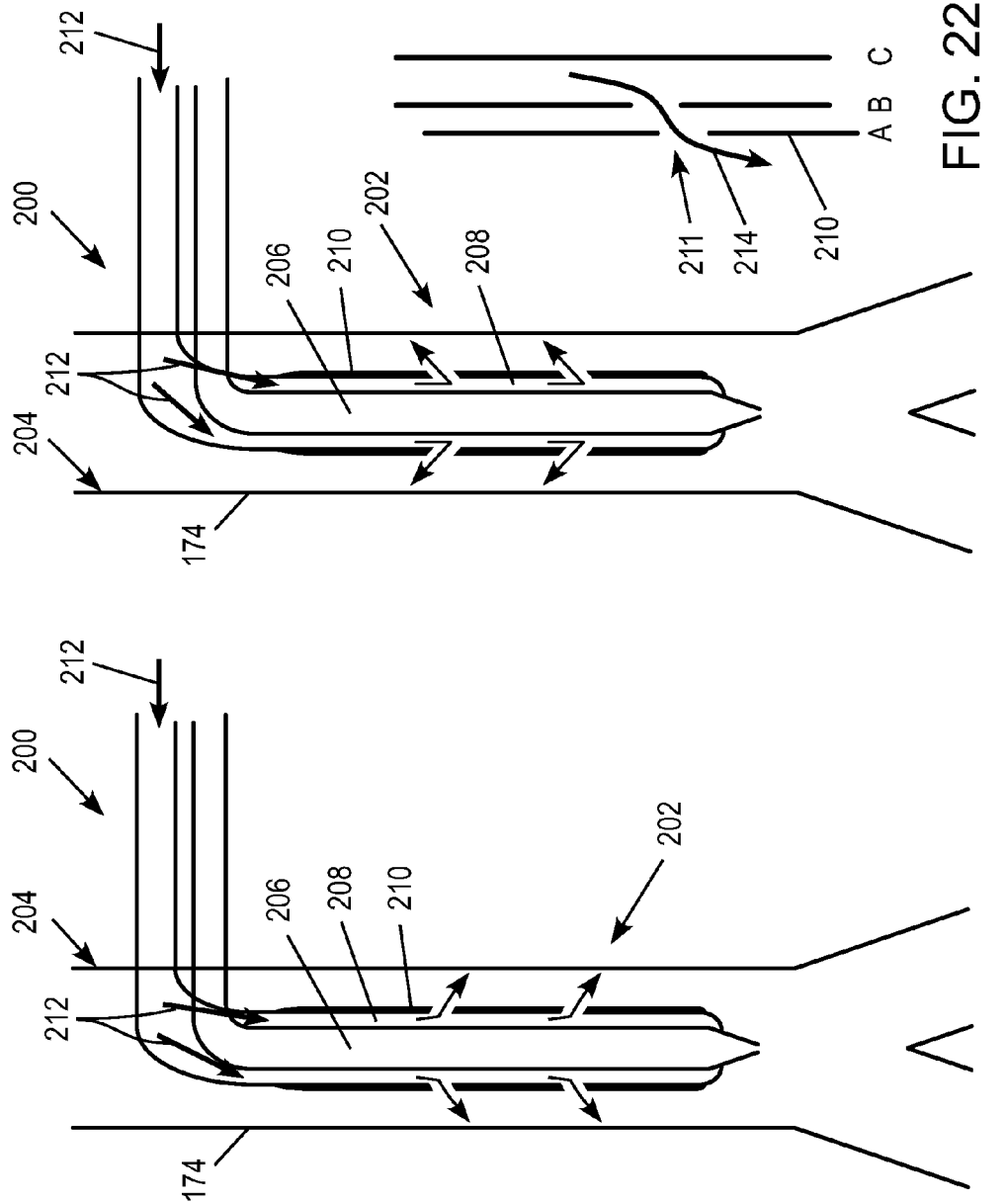

SYSTEMS, METHODS AND APPARATUS FOR RESPIRATORY SUPPORT OF A PATIENT

PRIORITY CLAIM

This application is a Continuation of U.S. application Ser. No. 11/523,519 filed Sep. 20, 2006 and issued as U.S. Pat. No. 7,33,670 on May 19, 2009, which claims the benefit of priority under 35 USC §§119 and 120 of U.S. Provisional Application No. 60/718,318 filed Sep. 20, 2005, the entire disclosure of each are hereby incorporated by reference.

FIELD OF INVENTION

The present invention relates generally to respiratory systems and more particularly to specialized systems, methods, and devices for enhanced ventilation of a patient.

BACKGROUND OF THE INVENTION

In order for the body to take in oxygen and give off carbon dioxide, two components of the respiratory bronchial system must function—the lungs as a gas-exchanging organ and the respiratory pump as a ventilation organ that transports air into the lungs and back out again. The breathing center in the brain, central and peripheral nerves, the osseous thorax and the breathing musculature as well as free, stable respiratory paths are necessary for a correct functioning of the respiratory pump.

In certain diseases there is a constant overload on or exhaustion of the respiratory pump. A typical syndrome is pulmonary emphysema with flat-standing diaphragms. Flat-standing diaphragms do not have the ability to contract. In the case of pulmonary emphysema, respiratory paths are usually extremely slack and tend to collapse. As a consequence of the flattened, over-extended diaphragms, the patient cannot inhale deeply enough. In addition, the patient cannot exhale sufficiently due to collapsing respiratory paths. This results in an insufficient respiration with an undersupply of oxygen and a rise of carbon dioxide in the blood, i.e. a ventilatory insufficiency.

The treatment for inhalation difficulty often involves a breathing device. A home ventilator is an artificial respirator for supporting or completely relieving the respiratory pump. Artificial respiration can be applied non-invasively via a nose or mouth mask that the patient can put on and take off as needed. However, the nose or mouth mask prevents the patient from breathing and speaking freely, and is very invasive.

Another treatment option is invasive ventilation. Invasive ventilation is usually applied via a cuffed endotracheal tube that is passed through the mouth and the larynx and into the windpipe, or is applied via a tracheostomy. The tracheostomy involves an opening placed in the trachea by an operation. A catheter about the diameter of a finger with a blocking balloon or cuff is inserted via the opening into the trachea and connected to a ventilator that applies cyclic positive pressure. This procedure makes sufficiently deep respiration possible, but prevents the patient from speaking.

In addition to home ventilation with a mask and invasive ventilation, there is also transtracheal administration of oxygen via thinner catheters. U.S. Pat. Nos. 5,181,509 or 5,279,288 disclose corresponding embodiments. In this manner, a highly dosed administration of oxygen is administered to the patient in a continuous stream with a permanently adjusted frequency. The flow rate of oxygen is regulated manually by a regulator. However, simulation of the natural breathing process of a patient is not achieved because the depth of breathing is not enhanced. Some common problems associated with these transtracheal catheters are irritations and traumas of the sensitive inner skin of the windpipe (tracheal mucosa). It is a common observation that the tip of the small catheter strikes against the inner wall of trachea as a consequence of the respiratory movement. In addition to this mechanical trauma, the surrounding tissue is dried out by the high flow oxygen stream.

Furthermore, so-called "Montgomery T-tubes" can be inserted into the trachea and a patient can obtain oxygen via a shank of the T-piece external to the patient. In needed, the patient can draw off secretions using a suction catheter and a vacuum pump. The patient can breathe freely and speak when the front shank is closed; however, normal artificial positive pressure ventilation is not possible via the Montgomery T-tube since the introduced air escapes upward into the oral cavity or the pharyngeal area. An additional limitation of the above-referenced therapies is the impaired mobility of the patient because of inadequate ventilation or because of the bulk of the apparatuses.

Jet ventilators are state of the art, but these devices are not synchronized with a patient's breathing. On the other hand, invasive ventilators with cuffed tubes are synchronized because there is a direct feedback of the pressure inside the inflated lung to the sensors inside the respirator. However, there are no respiratory systems that use feedback from sensors in the body to properly synchronize and control the ventilator.

Whether the breathing disorder is COPD/emphysema, fibrosis, sleep apnea, or otherwise, difficult breathing is a serious, often life-threatening problem. Therefore, there is an existing need for a respiratory system that provides a more efficient method for supporting the respiration of a patient that can be used to treat many disorders, are minimally invasive, mobile and taken along by the patient, and/or reliable in use. Moreover, there is a need for respiratory support systems that simulate the patient's spontaneous respiration without adversely affecting the patient's ability to speak. Additionally, there is a need for a respiratory support system capable of using pressure or flow signals from inside the body to properly synchronize and control a ventilator.

SUMMARY OF EXEMPLARY EMBODIMENTS

The invention includes systems, methods, and apparatuses that improve the quality of life for patients that require respiratory support. These respiratory systems, methods, and apparatuses can provide a more efficient way of supporting the respiration of a patient by providing additional oxygen when needed in accordance with the principles of the invention.

In one embodiment, a tracheal prosthesis and a catheter in accordance with the principles of the invention can provide for respiratory support that can be synchronized with the spontaneous respiration of the patient and still allow the patient to speak.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE FIGURES

The accompanying drawings, which are included to provide a further understanding of the invention, are incorporated in and constitute a part of this specification, illustrate preferred embodiments of the invention and together with the detailed description serve to explain the principles of the invention.

In the drawings:

FIG. 17 shows an embodiment of a dual lumen catheter in accordance with the invention.

FIG. 18 shows an embodiment of the flow through the catheter of FIG. 17 during inspiration in accordance with the principles of the invention.

FIG. 19 shows an embodiment of the flow through the catheter of FIG. 17 during expiration in accordance with the principles of the invention.

FIG. 20 shows an embodiment of a dual lumen catheter having a gliding wall in accordance with the invention.

FIG. 21 shows the catheter of FIG. 20 with the gliding wall in a different position.

FIG. 22 shows an expanded view of an air outlet of the catheter in FIG. 20.

FIG. 23 shows an expanded view of an air outlet of the catheter in FIG. 21.

DETAILED DESCRIPTION OF PREFERRED EMBODIMENTS

The present invention, in a preferred embodiment, provides systems, methods, and apparatus for supporting the respiration of a patient. This can be accomplished by providing controlled synchronized ventilation with a directed flow of an oxygen-bearing gas. The oxygen-bearing gas may be substantially pure oxygen, mixtures of oxygen and nitrogen, mixtures of oxygen and inert gases, ambient air, or various combinations thereof. In addition, the oxygen-bearing gas may include fragrances, aerosolized drugs, humidification or heating. The oxygen-bearing gas can be provided as needed upon inhalation and/or expiration, preferably, based upon sensing of the patient's spontaneous breathing.

By providing a jet boost of an oxygen-bearing gas upon inspiration, as needed, the patient can inhale more oxygen. Preferably, the additional oxygen is administered at the end of inhalation, in particular, after the peak of inspiratory flow is detected. The administration of additional oxygen can improve the depth of ventilation during inhalation. However, the additional oxygen may be administered at any point during inhalation. Additionally, a countercurrent or counter pulse during expiration can be delivered, which creates a back-pressure in the airways similar to the pursed lips breathing strategy applied by physiotherapists in order to avoid a collapse of the respiration paths. By providing an oxygen-bearing gas upon expiration through counter pulses (e.g. bursts or pulses of oxygen-bearing gas directed against the direction of the flow during expiration), a dynamic collapse of the airways can be minimized or prevented, over inflation of the lung can be minimized, and clearance of carbon dioxide from the lungs can be improved. Therefore, in accordance with the principles of the invention, whether used for inhalation and/or exhalation, breathing requires less energy and the patient's pain, dyspnea and exhaustion are relieved. Moreover, the systems and methods of the invention can be used for treatment of many breathing disorders, including, but not limited to, COPD, emphysema, fibrosis, and sleep apnea.

Figure 1A:
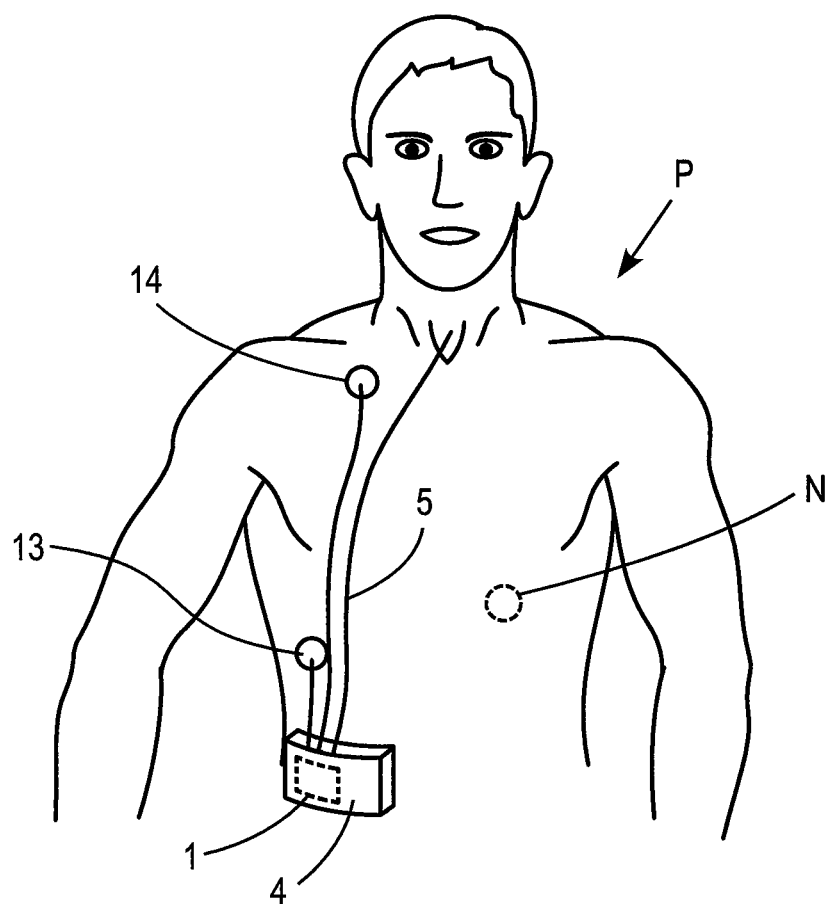
FIGS. 1A, 1B and 1C show a patient with embodiments of a system for respiration support in accordance with the principles of the invention.

Referring to FIG. 1A, in accordance with one embodiment of the invention, patient P designates a patient suffering from a breathing disorder, for example, pulmonary emphysema, with overloading and exhaustion of the respiratory muscles. As a consequence, the patient cannot inhale enough oxygen because the lungs are compromised. In addition, the patient cannot exhale enough carbon dioxide because the patient has slack and collapsing respiratory paths. The system of FIG. 1A generally includes the ability to detect the patient's spontaneous respiration and the ability to provide oxygen to the lungs of the patient during spontaneous inspiration and/or exhalation.

Figure 13:
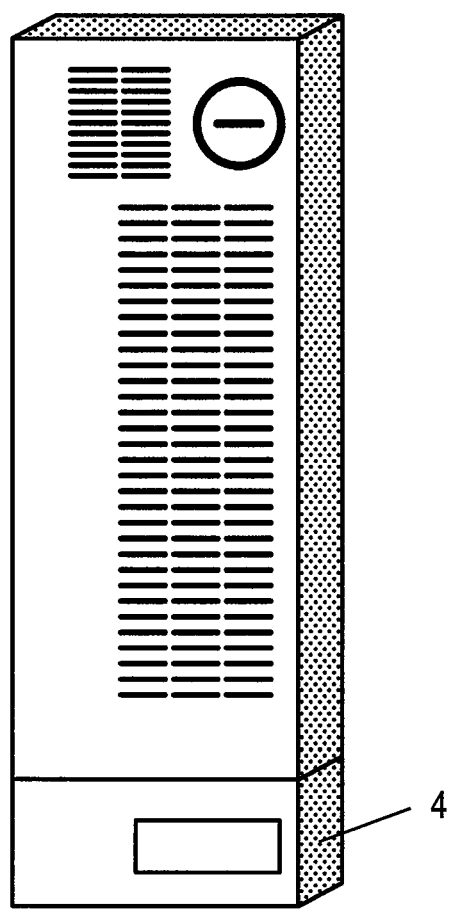
FIG. 13 shows a system in accordance with an embodiment of the invention where the pump and control unit are integrated with the oxygen tank.
Figure 25:
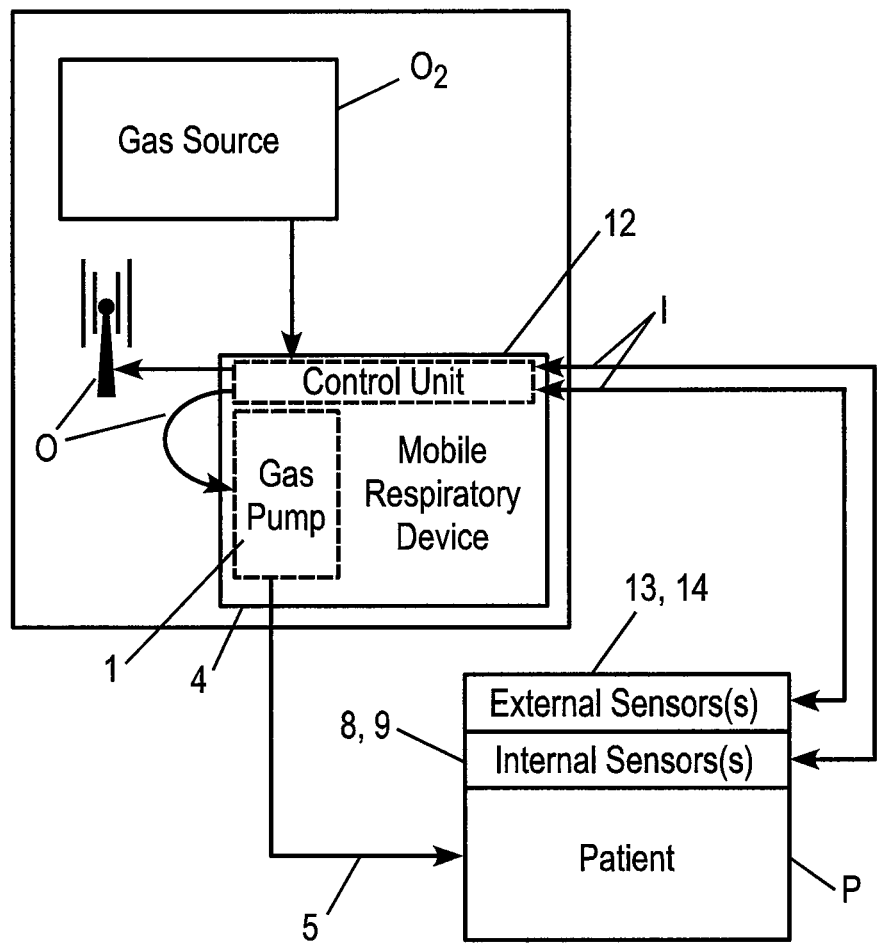
FIG. 25 is a diagram of the overall system.

As shown, the respiration support of patient P in accordance with the principles of the invention can be implemented in a system, method, or apparatus that may be compact and/or portable. Other systems are contemplated including, for example, providing for use with a ventilator or oxygen source as shown in FIG. 13. The overall system of the invention is described in FIG. 25, indicating the gas source O2, the pump apparatus 1 and control system 12, the catheter 5 and internal sensors 8, 9 and the patient P. The gas source O2, pump apparatus 1 and control system 12 can be separate or integrated components of the system. The control unit 12 may be connected I to internal sensors 8, 9 and/or external sensors 13, 14.

Figure 1B:
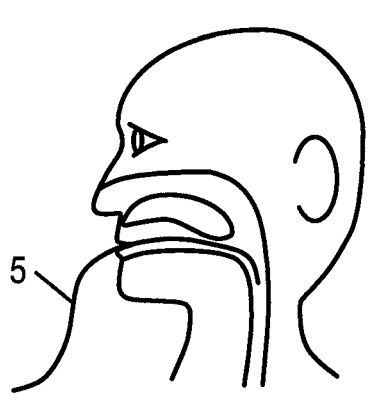
Figure 1C:
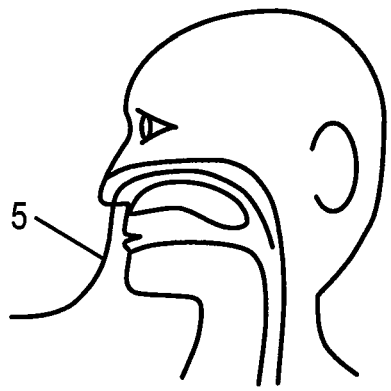

In accordance with the embodiment of FIG. 1A, in general, patient P's spontaneous breathing can be detected by way of sensors. A catheter 5 can be used to introduce oxygen into the lungs as needed. The sensors and catheter can be associated with the patient in a variety of ways. As illustrated in FIG. 1A, a catheter 5 is introduced in the trachea. Also, a catheter 5 could be introduced at other points into a patient P, including, for example, through the mouth (FIG. 1B) or nose (FIG. 1C) of the patient P, or accessed into the trachea by an artificially created entry point somewhere on the body and tunneled internally to and into the trachea. The catheter 5 can be secured in the trachea in a variety of ways. In one embodiment, the catheter 5 can be associated with a tracheal prosthesis as discussed later or using a positioning catheter as also discussed later with reference to FIGS. 3A, 3B and 4, for example.

Figure 2:
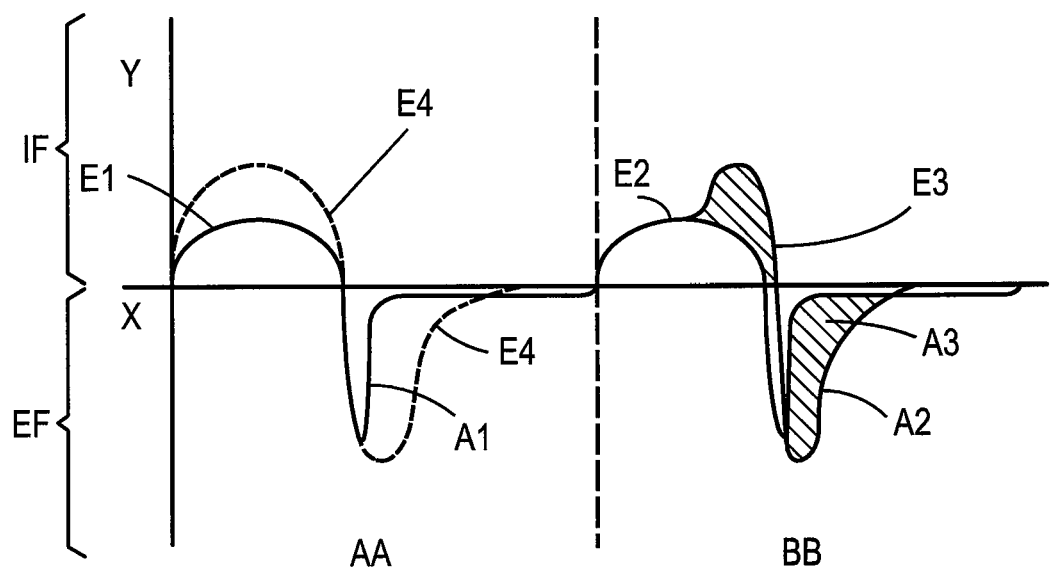
FIG. 2 shows a diagram with a view of the respiration flow of an emphysema patient without respiration support and with respiration support in accordance with the principles of the invention.

The system of FIG. 1A generally includes an oxygen-bearing gas source (not shown), gas pump 1, mobile respiratory device 4, also referred to as a ventilator, a set of exterior sensors 13, 14, and a set of interior sensors (not shown) disposed inside the trachea of the patient P. The oxygen-bearing gas pump 1 can be connected to a gas source (see FIG. 5) and catheter 5 to introduce an oxygen-bearing gas into the patient's lungs by way of the trachea, as shown, although other entry points can be used in accordance with the principles of the invention as discussed above. According to FIG. 1A, the oxygen-bearing gas pump 1 is shown as a component of a compact, easily portable respiration device 4. The device 4 could alternatively be housed in a component with a gas tank or oxygen-bearing gas source as illustrated in FIG. 13. With the sensors in accordance with the principles of the invention, the spontaneous respiration of the patient can be detected. Typically, the information from the sensors is communicated to the gas pump 1. However, the information from the sensors may also be communicated to a cellular telephone or other wireless systems that can communicate information to a healthcare provider/hospital, etc., for 24-hour monitoring and response from the healthcare provider/hospital, etc. The patient then can receive a pressure boost of oxygen-bearing gas as needed in accordance with the principles of the invention. FIG. 2 illustrates both spontaneous respiration of the patient P without the invention AA and respiration supported in accordance with the principles of the invention BB. The x-axis in this diagram represents time and the y-axis represents the amount of inspiratory flow IF and expiratory flow EF (change in volume over time) of oxygen-bearing gas, which can be liters per second or any other appropriate measurements. The spontaneous respiration process with inspiratory flow and expiratory flow without respiratory support for patient P is shown by AA in FIG. 2. The curve for inhalation is designated by E1 and the curve for exhalation by A1. As illustrated by curve E1, during inhalation the tidal volume inhaled is reduced from that of a normal patient E4. For example, a patient with emphysema with flattened diaphragms or a patient with stiff lungs suffering from fibrosis cannot breathe in enough air (oxygen) in one breath. Both patients typically experience shallow breathing. Therefore, the patient requires more breathing cycles to get the requisite amount of oxygen and clear carbon dioxide. During exhalation, as illustrated by curve A1, the expiratory flow of the emphysema patient is reduced because the respiratory paths can be slack and tend to collapse before an adequate amount of carbon dioxide is expelled from the lungs, compared to a normal patient E4.

The sensors allow the patient P's breathing to be monitored continuously so that a jet flow of oxygen-bearing gas can be supplied in accordance with the principles of the invention, that is, when a deeper breath is needed. In particular, at the end of an inhalation process of the lungs, an additional volume (oxygen) can be administered to patient P, as discussed in more detail below. This respiratory flow is illustrated in the right half of FIG. 2. As illustrated, an additional amount of oxygen-bearing gas provided to patient P increases the respiratory volume during inhalation according to curve E2 by the volume difference shown darkened in the upper curve and designated by E3. The additional amount of oxygen-bearing gas can have an extra space tidal volume between 25 ml and 150 ml.

In addition, the exhalation process of the patient can be braked or slowed by a countercurrent. As a consequence thereof, the respiratory flow shifts during exhalation along the curve designated by A2. This purposeful resistance acting opposite to the exhalation prevents a collapsing of the respiratory paths during exhalation. In this manner, the exhalation volume can be increased by the volume also shown darkened and designated by A3. The amount of carbon dioxide that is exhaled can be increased by a statistically significant amount. The amount of carbon dioxide that is exhaled can be increased by at least 5%. Preferably, the amount of carbon dioxide exhaled is increased from 5% to 30%. More preferably, the amount of carbon dioxide exhaled is increased about 20% to 30%.

As a consequence, the invention may avoid insufficient respiration from an undersupply of oxygen and an increase of carbon dioxide in the blood. The patient P may be significantly less stressed and more mobile, and may perceive less or no shortage of air.

The sensors for detecting and monitoring respiration will now be discussed in more detail. To detect spontaneous respiration of the patient P, sensors can be associated with an end of the catheter that is disposed in the trachea of the patient P. In one embodiment, the invention can include connecting the catheter to a tracheal prosthesis (e.g. FIGS. 3, 4, and 7) or can include a catheter-positioning device (e.g. FIGS. 14, 15, and 16A-16E) to more reliably and accurately direct the oxygen flow into the patient's airways and away from a tracheal wall. Preferably, in accordance with the principles of the invention, oxygen is introduced into the patient P in such a manner that the patient P can freely breathe and speak without restriction.

Figure 3A:
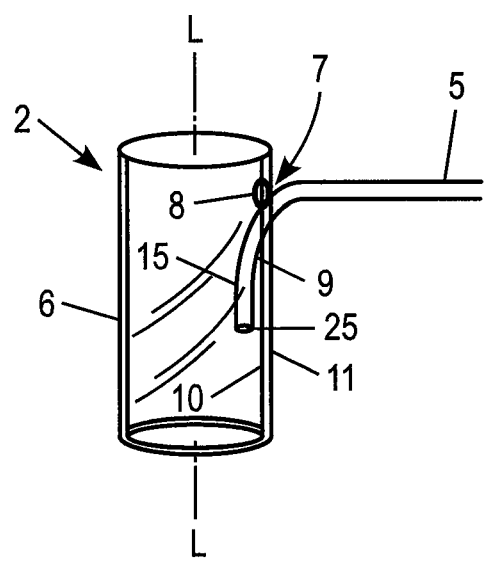
FIGS. 3A and 3B show technically simplified views of embodiments of tracheal prostheses in accordance with the principles of the invention.
Figure 4:
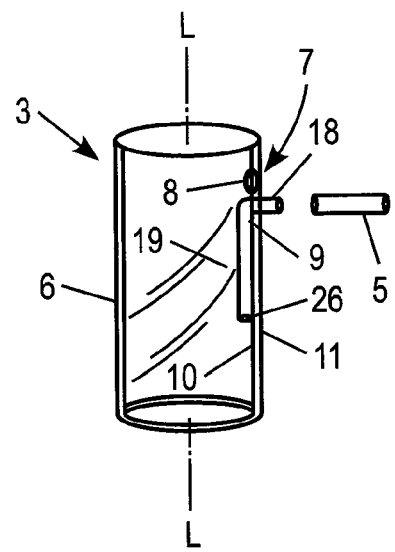
FIG. 4 shows another embodiment of a tracheal prosthesis in accordance with the principles of the invention.
Figure 5:
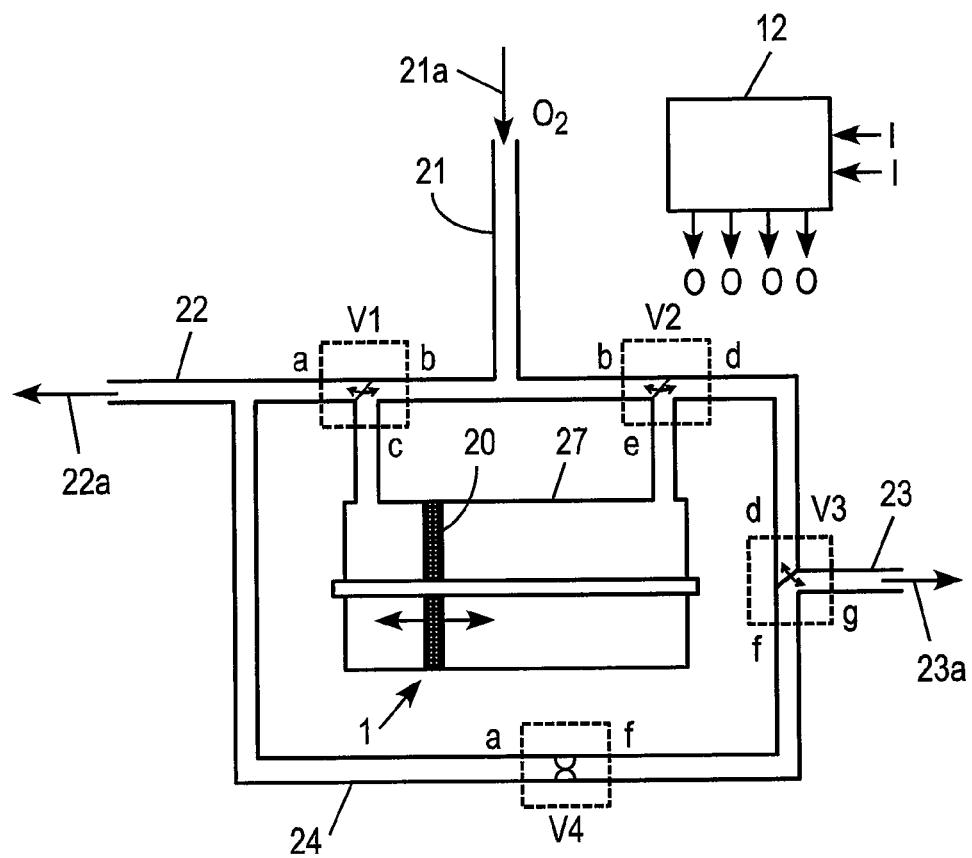
FIG. 5 shows a schematic of an embodiment of an oxygen-bearing gas tank and pump showing the conduction of air and a control unit in accordance with the principles of the invention.

In one embodiment, as shown in FIGS. 3A and 4, the sensors can be disposed on a tracheal prosthesis 2, 3. Each tracheal prosthesis 2, 3 is shown having a tubular support body 6 with a connection 7 for a catheter 5. As shown, two sensors 8, 9 detect spontaneous respiration of the patient P, and can be associated with a support body 6. The sensors 8, 9 can be thermistors, that is, temperature dependent resistors. The sensors 8, 9 can detect tracheal flow of the patient because inspired air and expired air have different temperatures. The thermistors 8, 9 can be connected together in a bridge circuit in the apparatus to compensate for changes in ambient air temperature. Other types of sensors can be used in accordance with the principles of the invention including, for example, a pressure sensor as discussed later. Both sensors 8, 9 can be located on an inner wall 10 of the support body 6 (FIG. 3A), or one sensor 8 can be fixed on the inner wall 10 of the support body 6 and the other sensor 9 can be located on an outer wall 11 of the support body 6 (FIG. 4). The sensors 8, 9 communicate with a control unit 12 for activating an oxygen jet pump 1. The sensors 8, 9 can be connected by wires or by wireless communication. The control unit 12 can be any type of microprocessor that is capable of processing the collected data in accordance with the invention. The control unit 12 is schematically shown in FIG. 5 with its inputs (I) and outputs (O). The inputs (I) represent information coming from the sensors. The outputs (O) represent information that is used to control the pump 1.

In the tracheal prosthesis 2 according to FIG. 3A, the jet catheter 5 can be inserted via connection 7 into the support body 6. An end 15 of jet catheter 5, located in support body 6, is preferably guided or deflected approximately parallel to its longitudinal axis L. The data lines from sensors 8, 9 to the control unit 12 run inside the catheter 5. The invention is not limited to data lines; transmission from sensors can be any type of transmission, including wireless. On the discharge side, the end 15 of the jet catheter 5 is preferably designed as a jet nozzle 25. The jet nozzle 25 increases the speed of an oxygen current being discharged from the catheter 5, and the current is conducted in the direction of the bronchial tract. The diameter of the support body 6 is dimensioned with a sufficiently free lumen in such a manner that the patient P can freely breathe and speak even with the integrated catheter 5.

In another embodiment, a separate coupling 18 is provided on the connection 7 in the tracheal prosthesis 3 according to FIG. 4. The catheter 5 can be connected to the tracheal prosthesis 3 with the separate coupling 18. In this instance, a fixed longitudinal section 19 aligned parallel to the longitudinal axis L can serve as the catheter end in the support body 6, and the oxygen current is conducted via a jet nozzle 26 in the direction of the bronchial tract.

Figure 3B:
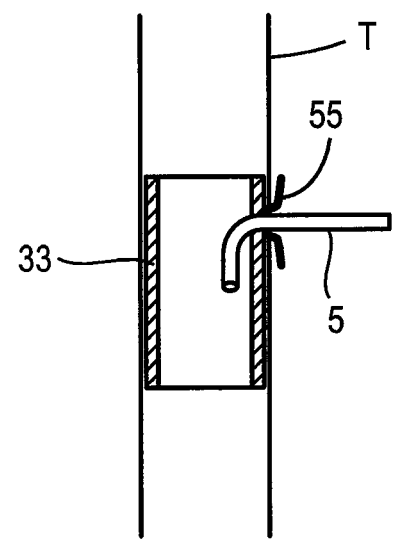

The tracheal prosthesis, when used, can comprise various configurations, shapes and dimensions. For example, the tube could be T-shaped or L-shaped or otherwise. The size, shape, and/or cross-section can vary, for example, to accommodate removal or to direct the catheter. The tracheal prosthesis could be a portion of a tube having, for example, a semi circular cross-section. Furthermore, expandable and self-expandable prongs or petals can be used at the tracheal opening to secure the prosthesis in place. In one embodiment, the prosthesis can include a tubular member with a tracheal side opening including prongs or petals surrounding, in whole or in part, the access hole. The prongs or petals 55, for example, of prosthesis 33 may function like a rivet in the neck opening (FIG. 3B). The tracheal prosthesis can also be coated to avoid mucus retention, prevent the formation of granulation tissue, or can act as a drug-releasing device. The tracheal prosthesis may also include other coatings, such as lubricious coatings and hydrogel anesthetics. Thus, the tracheal prosthesis can serve as a guide for the catheter, to hold sensing devices, serve as a drug delivery device, and/or to minimize mucus plugs that can form on the catheter tip.

In addition to internal sensors, external sensors can be provided. FIG. 1A also shows respiration sensors 13, 14, preferably, impedance electrodes or respibands. Signals from the sensors 13, 14 are also for detecting the spontaneous respiratory efforts of the patient P. An exact image of the respiration process of patient P can be obtained by processing the measured values received via sensors 8, 9 and 13, 14. In addition, the safety against false measurements or the failure of one of sensors 8, 9 and/or 13, 14 can be increased due to redundancy. Although the sensors are shown in certain locations on the patient P, other locations that would allow the sensor to sense the patient's respiration, directly or indirectly, can be used. For example, sensors can be provided on the catheter as discussed later. Alternatively, a pill-type sensor or nano device N (FIG. 1A) can be used and/or implanted to communicate by, for example, wireless transmission to communicate with the control unit to operate the oxygen flow through the catheter in accordance with the principles of the invention.

Figure 6:
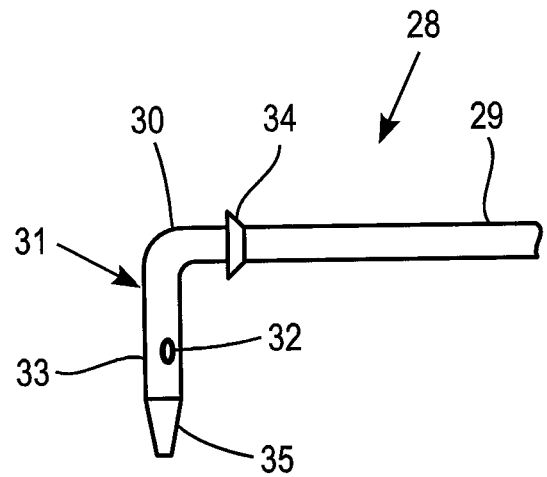
FIG. 6 shows an embodiment of the end section of a catheter in accordance with the principles of the invention.
Figure 7:
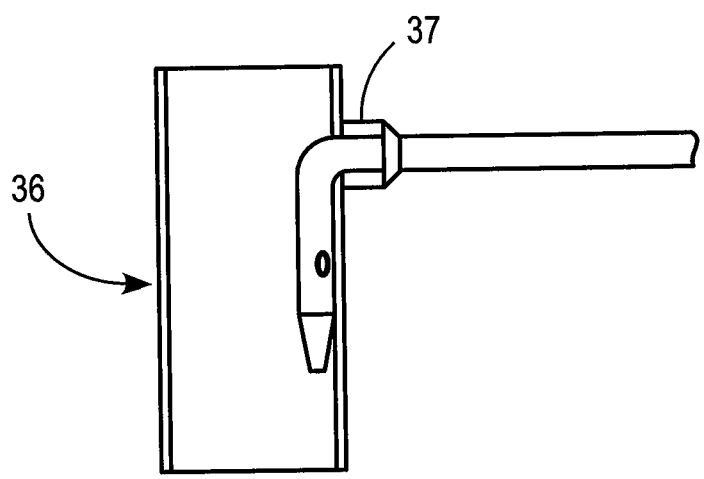
FIG. 7 shows the catheter according to FIG. 6 inserted in a support body in accordance with the principles of the invention.

One embodiment where sensors are provided on the catheter is shown in FIG. 6. FIG. 6 shows a catheter 28 with a long, flexible tube 29 and an end 31 on the discharge side bent in a curvature 30. The catheter 28 can be pre-formed to provide a desired curvature 30. With the appropriate curvature 30, the catheter 28 can be entered into the trachea with or without use of a prosthesis. In this embodiment, two sensors 32, 33 for detecting the spontaneous respiration of the patient P can be fastened on the end of the catheter 28. The sensors 32, 33 are preferably thermistors, but as in all embodiments herein, could be other types of sensors. Furthermore, in other embodiments of the invention, additional sensors may be used. In still other embodiments of the invention, fewer sensors may be used. Data lines are not shown in the drawing for the sake of simplicity and could include any form of data transmission. In a hard-wired embodiment, data lines can run through the catheter 28. A catheter flange 34 designates a stop for use with a support body 36, as shown in FIG. 7. It can also be seen that an end 31 of the catheter 28 is provided with a jet nozzle 35. The cross-section of gas flow is reduced relative to the cross-section of the catheter 28 in the jet nozzle 35 so that the discharge rate of the supplied oxygen is increased.

The catheter 28 can be introduced into the support body 36, as shown in FIG. 7. The support body 36 is located in the trachea of the patient P. A connection to the outside is established via a connection 37. In the body, the tip or jet nozzle end 35 of the catheter 28 can be disposed in the trachea. Preferably, the tip of the catheter 28 does not touch the tracheal wall. The support body 36 can be a traditional Montgomery T-stent.

Figure 8A:
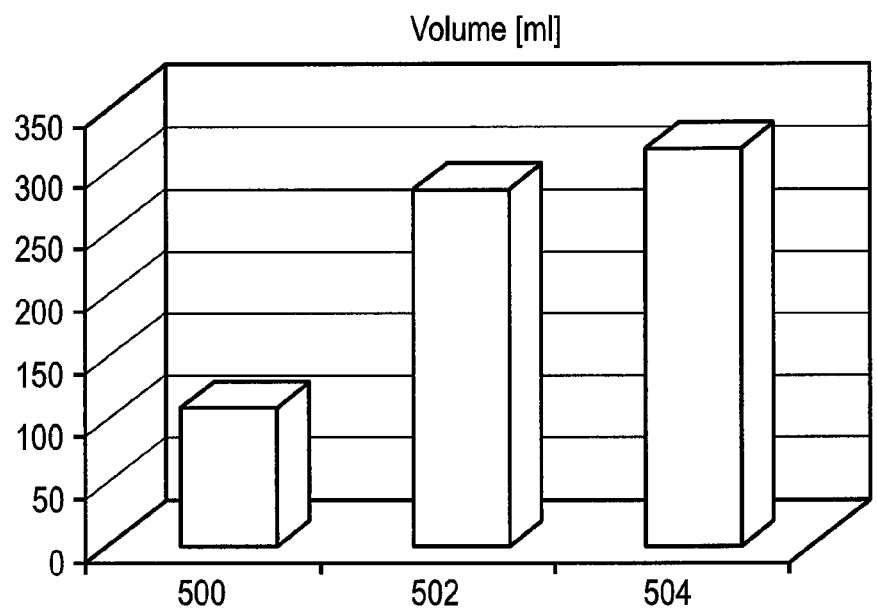
FIGS. 8A and 8B show graphs of breathing data generated from a bench model test in accordance with the principles of the invention.
Figure 8B:
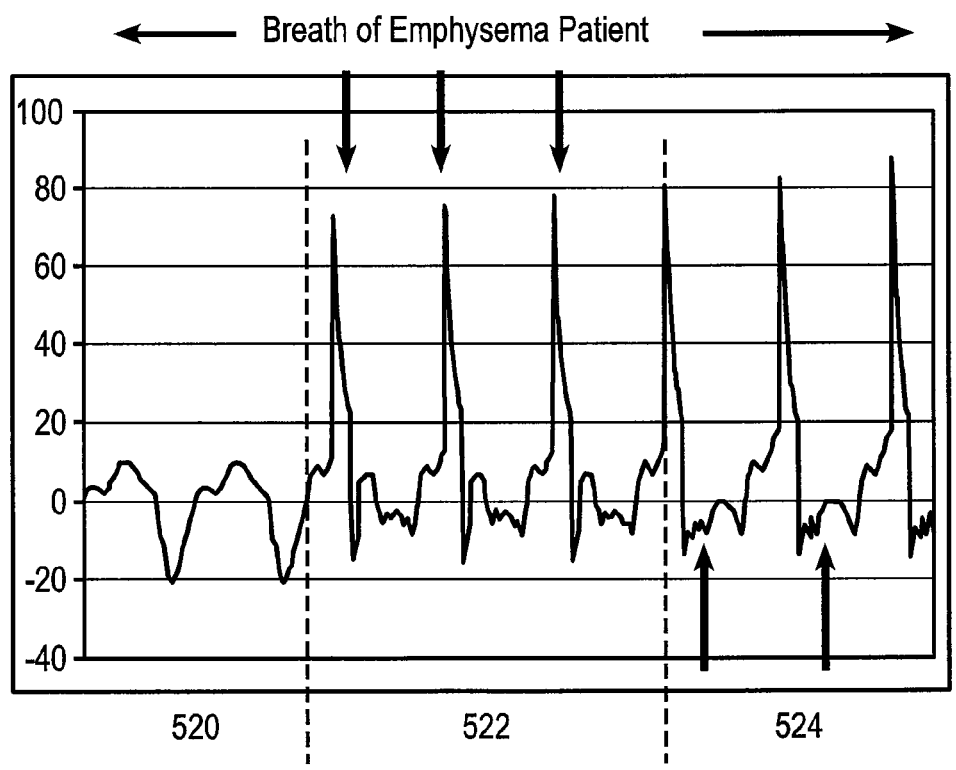

FIGS. 8A and 8B show measurements in a lung model emulating respiratory diseases. FIGS. 8A and 8B graphically illustrate an increased tidal volume with the invention. FIG. 8A shows a bar graph of the volume (ml) of breath comparing a pathologically low breath of a patient with emphysema at about 90 ml 500, that is the patient's "normal breath"; the volume with jet oxygen in accordance with the principles of the invention upon inhalation at about 260 ml 520, that is without therapy; and the volume with the jet oxygen in accordance with the principles of the invention upon inhalation 522, that is with inspiratory augmentation per the invention; and with the flow brake (oxygen jet) upon exhalation 524, that is without inspiratory augmentation and expiratory flow brake per the invention at about 300 ml. FIG. 8B shows a graph of the flow of breath (liters per second) over time for a breath of an emphysema patient; the flow with jet oxygen in accordance with the principles of the invention upon inhalation; and the flow with jet oxygen in accordance with the principles of the invention upon inhalation and with the flow brake (oxygen jet) upon exhalation.

Figure 10:
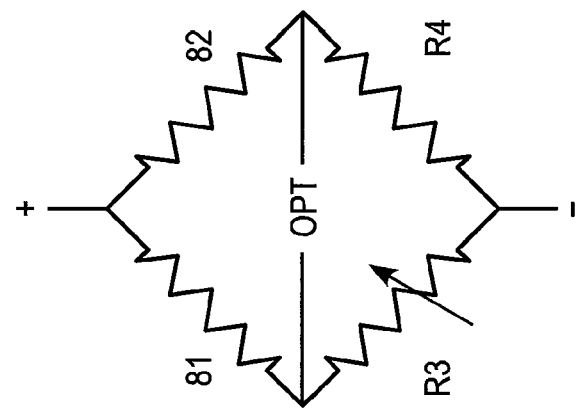
FIG. 10 shows a schematic of an embodiment of a circuit in accordance with the invention.
Figure 9:
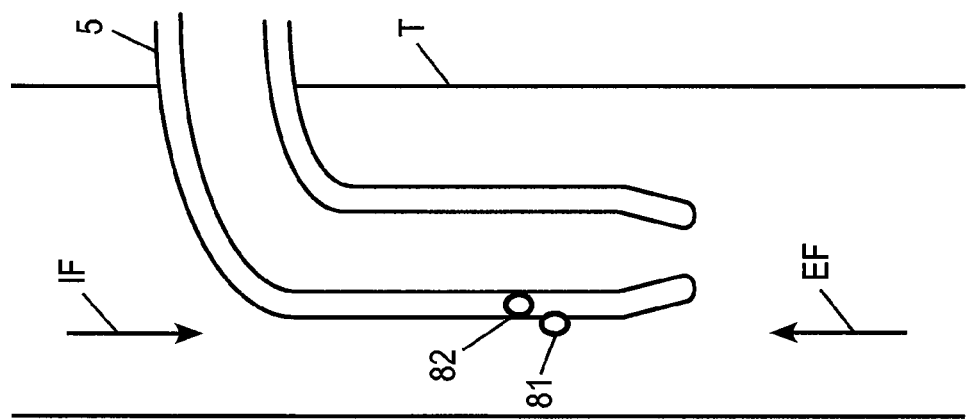
FIG. 9 shows an embodiment of a catheter and sensors in accordance with the invention.

In another embodiment shown in FIGS. 9 and 10, thermistors 81 and 82 can be provided on a catheter tip of catheter 5 inside the trachea T. The thermistor 81 is more exposed to the gas stream than thermistor 82, which is protected against fast temperature changes because it is inside the catheter wall (or under a protection film). FIG. 9 shows the in flow (IF) can be cold and the exit flow (EF) can be warm. Alternatively, multiple thermistors with different response times could be used. Over a longer period (e.g. 10 seconds), both mean temperatures will be the same (equilibrium) and the bridge (FIG. 10 showing thermistors 81 and 82, resistors R3 and R4, and output (OPT)) will be readjusted. This compensates for changes in ambient temperature, fever, etc. Rapid changes based upon breathing in colder air and breathing out warmer air is detected by the thermistor 81. The output signal is sent through a differentiator. The peaks of the thermistor signal match the highest flow rates. The minimum in the differentiated signal matches the peak of the inspiratory flow and the peak of the expiratory flow. Undifferentiated and differentiated signals are fed into the microprocessor. One way to determine peak inspiratory flow (trigger for beginning introduction of oxygen) would be to look for minimum in absolute temperature (cold air comes in) and zero change of temperature (differentiated signal is zero). The advantage of using the above multiple thermistor approach is that the difference between the signals from the two thermistors cancels out flow artifacts found in the measured respiratory flow pattern, such as would be caused by vibration or other anticipated events, and to compensate for drift in the thermistor signal such as would be caused by changing external or internal temperature or humidity conditions.

Figure 12:
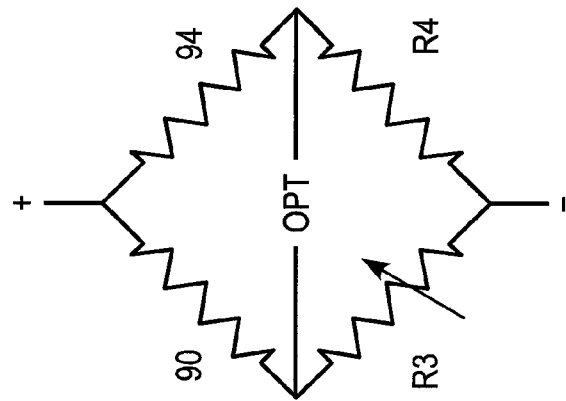
FIG. 12 shows a schematic of another circuit in accordance with the invention.
Figure 11:
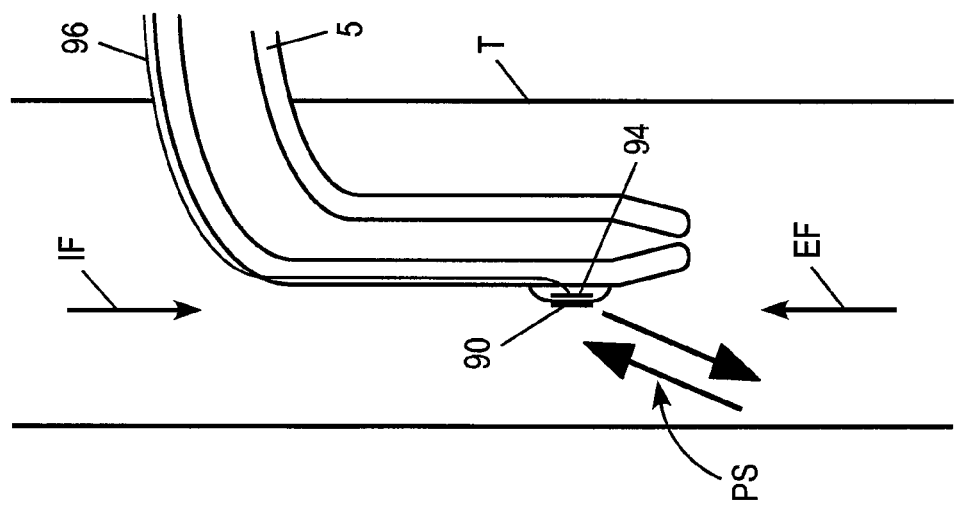
FIG. 11 shows another embodiment of a catheter and sensors in accordance with the invention.

In another embodiment, as shown in FIGS. 11 and 12, FIG. 11 shows a pressure transducer that is a modified silicone wire strain gauge element 90 (can be a wire strain gauge), 94 (can be a wire strain gauge). Instead of a typical silicone membrane, the wall of the catheter 5 is used. If the wall of the catheter deforms under the pressure swings PS inside the trachea (breathing effort), the signal is fed into the bridge circuit by electrical wire 96 (or wires), then an electrical signal from the bridge amplifier is fed into a microprocessor. This embodiment can be used alternatively to the thermistors, as a redundant signal or as a back-up signal. Other sensors could be semiconductor flow sensors or pressure sensors. FIG. 12 shows a circuit diagram of a bridge amplifier.

Other sensors can be used in accordance with the invention. For example, sensors and/or secondary control sensors could be: respibands (chest wall strain gages), respitrace signals (conductance plethysmographs), pressure sensors inside or outside the body, transthoracic electrical impedance measuring devices, flow sensors at the mouth or nose (pneumotachographs), and/or capnometers (carbon-dioxide sensors). Moreover, the sensors in accordance with the invention can communicate data or information to the control unit by any devices, mechanisms, or methods. For example, communication can occur by way of wire, wireless, or remote transmission. The advantage of using non-thermistor sensors is that the thermistor approach may have the disadvantage of the thermistor head collecting airway mucus, which could be corrected for in a variety of ways such as with cleaning. However, other non-thermistor sensors may be less susceptible to annoyances like mucus collection. Further, with thermistor sensors, inevitable changes in ambient temperature, while compensatable in the thermistor signal processing algorithms, are potentially problematic to system reliability. Therefore, the other types of sensors stated above may be advantageous over thermistor sensors, or in addition to the thermistor sensors.

In addition to measuring the respiration pattern, it is often desirable to measure airway pressure for safety reasons, for which thermistor sensors may not be the best approach. Therefore, some of the sensors mentioned above can also be used as a safety control device. For example, pressure sensors can be used to sense the inspiration of the patient (like the thermistors), but they can also be used to sense a high pressure in the trachea and shut off the jet machine in order to prevent baro-trauma (damage from high pressure).

An oxygen-bearing gas is provided on demand by the gas pump 1. The gas pump 1 is schematically shown in FIG. 5. The gas pump 1 can be a piston pump with a double-acting piston 20 arranged in a cylinder 27. The piston pump of the present embodiment comprises four valves V1 to V4. Other piston pumps (not shown) may have greater than or fewer than four valves. The supply of oxygen ($O_2$) emanates from an external oxygen reservoir via a connection 21. Reference 21$a$ shows the in flow of oxygen, reference 22$a$ shows the outflow (E3) of oxygen to the catheter, and 23$a$ shows out exhaust. The switching states of valves V1 to V4 and the supply lines and removal lines are designated by letters a to g. Other types of pumps can be used in accordance with the principles of the invention.

The gas pump 1 functions in the apparatus during the support of respiration as follows. When valve V1 is open from c to a (b to c closed) and valve V2 is open from b to e (e to d closed), piston 20 moves to the left in the plane of the figure and the oxygen flows via outlet 22 and jet catheter 5 to the patient P. An additional amount of oxygen E3 is administered during the inhalation process of the patient P.

When valve V1 is open from b to c (c to a closed) and valve V2 is open from e to d (b to e closed), piston 20 moves to the right in the plane of the figure and the flow of oxygen takes place in the direction of valve V3. Valve V3 is connected to the ambient air via an outlet 23. In the instance in which valve V3 is open from d to g, the oxygen flows off without expiration brake. That means that the exhalation process is not braked by a countercurrent.

If valve V3 is closed from d to g and open from d to f, the oxygen flows via access path 24 in the direction of the outlet 22 and the catheter 5 in order to be administered to the patient P during the exhalation process and in order to break the respiratory flow. The countercurrent prevents a collapsing of the respiratory paths and keeps them open, making a deeper exhalation possible.

Furthermore, valve V4 is located in access path 24 of the apparatus, via which the flow through (f to a) can be variably adjusted. This advantageously can be a proportional valve with pulse-width modulation.

As discussed above, the catheter preferably includes a jet nozzle. Any type of jet nozzle can be used to achieve the necessary jet flow. The jet flow speed in accordance with the invention can be significantly higher than 100 m/s. By comparison, the speed through a conventional ventilator tube or mask is significantly lower than 100 m/s. When the jet flow rate is high enough, there is enough speed so that directed flow is accomplished and no sealing tube cuff would be necessary. Under normal ventilation, the volumetric inspiratory flow rate is in the range of about 500 $cm^3$ to 1000 $cm^3$ in 2 seconds. A peak inspiratory flow maximum can be 1000 $cm^3$/second. In the case of normal invasive ventilation, the flow of 1000 $cm^3$/s (peak) goes through a tube of approximately 8 mm diameter. The speed of this gas stream, determined by dividing the volumetric inspiratory flow rate by the area of the tube, is 1000 $cm^3$/$(0.4)^2$ $cm^2$*Pi=2000 cm/s=20 m/s. During jet ventilation, approximately half of this flow goes through a jet cannula of 1.5 mm diameter. As the flow profile is rectangular, the peak flow rate is 500 $cm^3$/s. Therefore, the speed of the jet gas stream is 500 $cm^3$/$(0.075)^2$ $cm^2$*Pi=28313 cm/s=283 m/s. In accordance with a preferred embodiment of the invention, 100 ml ($cm^3$) are pressed through a catheter of approx 1.5 mm diameter in half a second. Preferably, the peak flow for this embodiment is 100 $cm^3$ in 0.25 seconds=400 $cm^3$/s. The speed of this gas stream is 400 $cm^3$/$(0.075)_2$ $cm^2$*Pi=22650 cm/s=226 m/s. In other preferred embodiments, the speed of the gas stream is from approximately 100 m/s to approximately 300 m/s. Preferably, the speed of the gas stream is from approximately 200 m/s to approximately 300 m/s. Preferably, the speed of the gas stream is from approximately 250 m/s to approximately 300 m/s.

Figure 14:
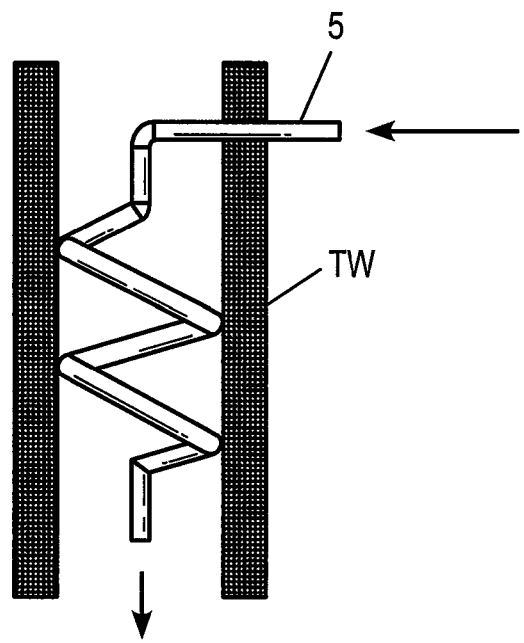
FIG. 14 shows an embodiment of a distal end of a catheter in accordance with the invention.
Figure 15:
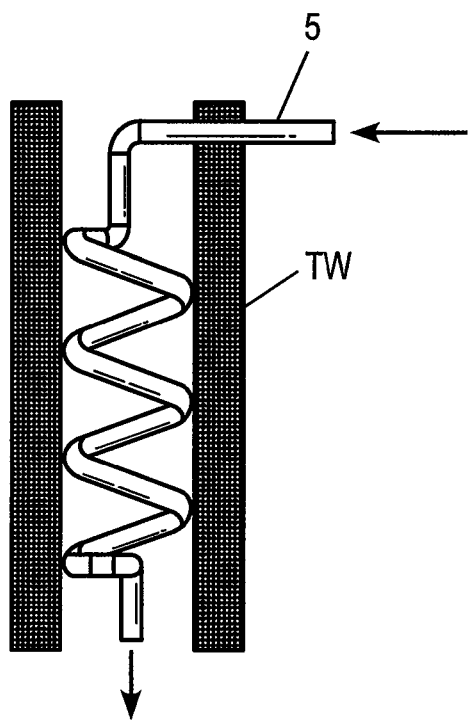
FIG. 15 shows another embodiment of a distal end of a catheter in accordance with the invention.

When the tip of the catheter touches the wall of the trachea TW (FIGS. 14 and 15), there is a potential risk of tissue damage. The catheter tip or the high flow gas stream can harm the mucosa. To efficiently and effectively direct the air inside the body, the catheter can be configured to provide a directed flow of oxygen. In particular, the catheter is preferably configured so that the exit of air from the catheter output end can expel and direct air down the center of the trachea to avoid directing the jet flow of oxygen against the tracheal wall. Also, the catheter tips are preferably configured to minimize venturi and the mucus formation proximal to the venturi on the outer wall of the catheter. A shielding Montgomery T-tube as described above can be used to overcome that problem. In FIGS. 14 and 15, the catheters are configured such that the catheter tip or jet nozzle avoids contact with the wall of the trachea TW; the tip is substantially centered in the trachea. This can be accomplished by configuring the catheter so that the catheter will contact the tracheal wall at several locations to distribute the local pressure, and the tip where the jet flow of oxygen exits the catheter is substantially centered in the trachea. Accordingly, the use of a tracheal prosthesis is not necessary. One way to avoid the contact between the tip (jet nozzle) and the airway wall is to bend the catheter like a zigzag in two planes or bending in two dimensions as illustrated in FIG. 14. Another embodiment is a corkscrew or coil as illustrated in FIG. 15.

Figure 16A:
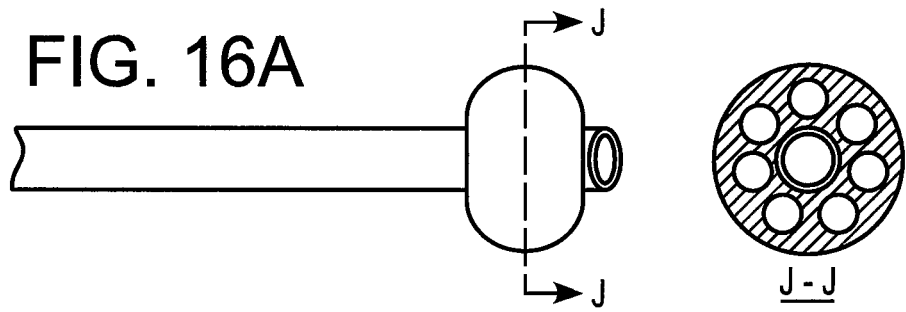
FIGS. 16A-16E shows embodiments of a catheter in accordance with the invention.
Figure 16B:
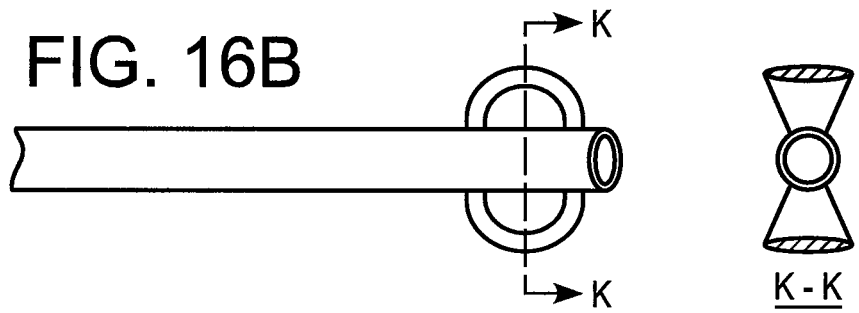
Figure 16C:
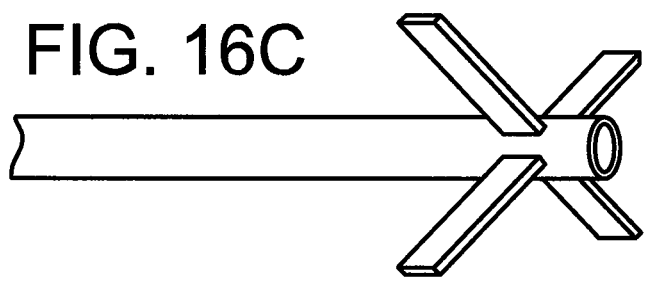
Figure 16D:
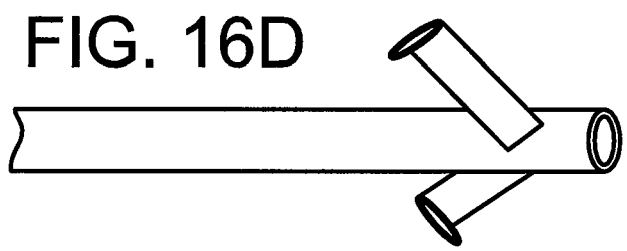
Figure 16E:
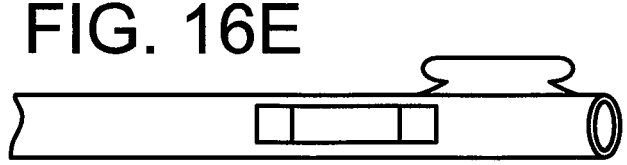

FIGS. 16A-16E show alternate embodiments for centering the catheter where balloons (FIGS. 16A and 16B) or clips (FIGS. 16C-16E) can be used to center the catheter tip. FIG. 16A shows a balloon for centering the catheter tip where the balloon has a roughly circular cross section through line J-J. Openings in the balloon may be located in the longitudinal direction of the catheter. FIG. 16B shows a balloon for centering the catheter tip where the balloon can have multiple extensions. The extensions may appear as cone-shaped projections in cross section K-K along the longitudinal direction of the catheter. FIG. 16C shows clips extending radially out from the catheter. The clips in this embodiment are relatively flat and extend outward in opposing pairs. FIG. 16D shows another embodiment of clips with extensions on the end of the clips. The clips and extensions may extend at multiple angles relative to the catheter for centering the catheter tip within the trachea. FIG. 16E shows another embodiment of clips having shaped protrusions at various locations along the length of the catheter. The protrusions may have flat tops with rounded edges and undercuts. Preferably, the clips of the various embodiments are made of a resilient material.

Referring now to FIGS. 17-23, a dual lumen catheter will be described. The invention can also include the ability to better distribute the directed flow (FIGS. 17-19) and/or change the direction of the flow (FIGS. 20-23). FIGS. 17-19 show a dual lumen catheter 172. The catheter tip, shown generally at 170, is disposed in a trachea 174. The catheter 172 has two lumens, formed by inner cannula 176 and outer cannula 178. Outer cannula 178 can be for "flow-disturbing flow." Inner cannula 176 directs flow to a catheter nozzle 180, as discussed above and can be an inner jet-cannula for "flow-directed-flow."[[.]] As shown in FIG. 18, upon inspiration, inspired flow is enhanced by air entrainment 191 from the jet flow through the inner cannula plus by the jet flow itself 190. inspiration flow is enhanced by additional jet flow through inner cannula 176. Upon expiration (FIG. 19), exhaled flow 196 is enhanced by turbulence 198 from counter flow 194 through ports 182 by means of propping the respiratory paths open. Expiration flow is attenuated by turbulences from counter flow through outer cannula 178. The ports 182 need not be of any particular shape and may be, for example, circular, hexagonal, oval, or slits. Although not shown, turbulent flow could also be provided through inner cannula 176 during exhalation to enhance exhaled flow depending upon the desired effect.

Referring to FIGS. 20-23, another embodiment of a catheter is shown, the patient is provided expiration flow braking turbulence or additional venture flow towards the mouth depending upon the state of the gliding wall filaments of the catheter. A catheter 200 is shown with a distal tip 202 in a trachea 174. The catheter tip 202 includes a cannula configuration with an inner lumen 206, an outer lumen 208 concentric to the inner lumen, and a gliding sheath 210. In this embodiment, the gliding sheath 210 moves relative to the cannula to allow ports 211 to change the direction of oxygen flow 212 as illustrated in FIG. 20 verses FIG. 21, and in close-up in FIG. 22 verses FIG. 23. As shown in FIG. 22, upon expiration, the flow braking turbulence 214, (FIG. 22) caused by movement of the gliding sheath 210 may create a resistance such as in pursed-lip breathing, which can prop the respiratory paths open to enhance the amount of exhaled volume. Or, as shown in FIG. 23, the addition of venturi flow towards the mouth 216 caused by movement of the gliding sheath 210 can entrain exhaled flow to enhance the overall exhaled volume. Although the gliding sheath 210 is shown to move, more or other parts can be made to move to accomplish the directed flow of this embodiment. For example, flow braking turbulence or venturi flow toward the mouth may be produced by the use of shutters, louvers, or slats.

Regardless, the flow can be directed towards the mouth or back into the lungs as desired. The flow brake for the expiratory flow of the patient can be adjusted from disturbance (pursed lips effect) or to augmentation (venturi principle). The whole catheter preferably does not have more than 4 mm outer diameter, but can be very versatile. This embodiment, like the other embodiments of the invention, can also be used to apply vibratory flow to the respiratory paths to improve mucus clearance.

The system in accordance with the principles of the invention can be implantable. In one embodiment, the system including the jet catheter and system sensors can be implanted inside the body. Although it is possible to implant the pump, it is contemplated that tubing attached to the pump can be connected to a connector exposed from the body. The pump tubing can be attached to the connector in a conventional manner so that the oxygen-bearing gas flows through the implanted jet catheters into the patient in accordance with the principles of the invention. The system can be tailored to the needs of the patient. The jet pressure and timing and duration of the pulses can be monitored and controlled and adjusted as necessary based on the patient's respiratory condition and general status. As shown in FIG. 1A, the catheter can extend along the outside of the body. Alternatively, the catheter could be implanted inside the patient's body. For example, the catheter could have one exposed end for connection with the pump and some or all of the remainder of the catheter could be implanted inside the patient and/or under the skin of the patient. The output end of the catheter could, for example, be exposed for connection to the tracheal prosthesis or positioned in the nose or mouth. Furthermore, the portion of the catheter disposed in the patient can be treated. For example, it can be treated with an antibacterial, a drug, a lubricious coating, a treatment to prevent mucous formation, or otherwise.

Figure 24:
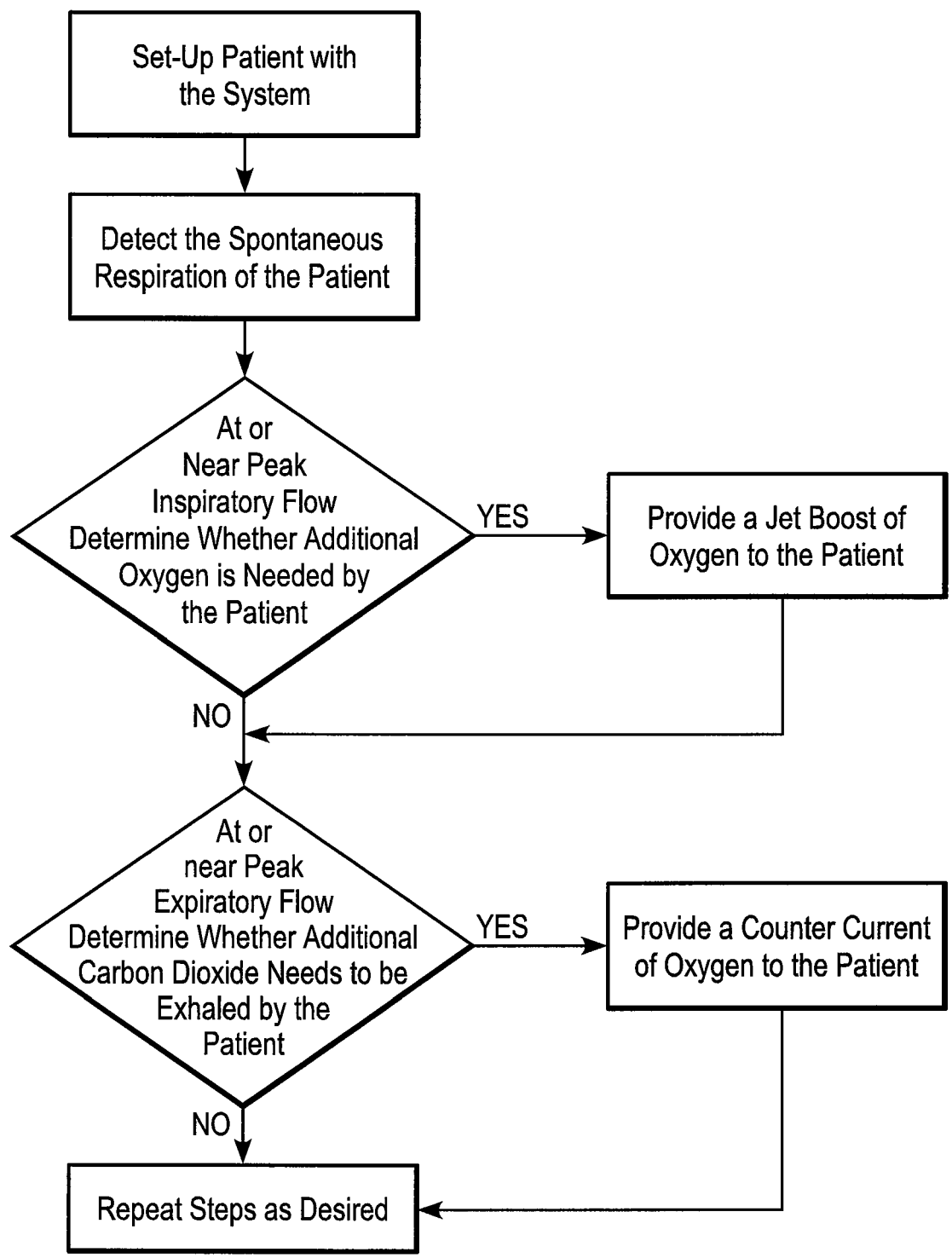
FIG. 24 is a flow diagram illustrating the operation of an embodiment of the invention.

FIG. 24 is a flow diagram illustrating an embodiment of a method of the invention. In accordance with this embodiment of the invention, the patient is provided with the system in accordance with the invention. The system is used to detect the spontaneous respiration of the patient. At or near the peak of inspiration flow, the system determines whether additional oxygen is needed by the patient. If yes, the system provides a jet boost of oxygen to the patient. Then at or near the peak of expiration flow, the system determines whether more carbon dioxide must be exhaled by the patient. If more must be exhaled, then the system provides a counter current of oxygen to the patient. The process is repeated as needed. The advantage of this embodiment is to allow the therapy to match the needs of the patient. Other ventilator systems tend to apply a predetermined therapy regardless of the changing condition of the patient, until a clinician changes a setting on the ventilator. Other ventilator systems are therapeutically suboptimal for a wide range of patient situations, often leading to over treatment, making the patient too dependent on artificial ventilation, or leading to under treatment, and thus worsening the patient's clinical condition. Therefore, in accordance with this invention the ventilator will adjust an output to the patient based on the patient's need. The ventilator can make a determination by using patient information already obtained by the sensors, such as breath rate, depth of respiration, length of inspiration or exhalation, agitation, or gas concentration levels. For example, if a patient is exercising and an unusually low exhalation flow rate is detected by the sensors, indicating that airways are collapsing too much during exhalation, then, exhalation counter flow could be switched on or increased to prop the airways open and enhance exhaled flow. Or, for example, if the patient's breathing becomes unusually fast as measured by the breath sensors, indicating the patient is compensating for shortness of breath, the inspiratory augmentation pulse could be switched on or increased to relieve the patient's dyspnea. Or as another example, gas composition sensors detecting $CO_2$ and $O_2$ levels in the airway can determine if the therapy is adequate and increase or lower the therapy as needed.

As mentioned above, the principles of the invention can be used in treating and/or assisting in the treatment of a variety of breathing disorders and/or breathing difficulties. In such treatments, the invention can provide an oxygen-bearing gas into any of the airways of the patient. In one such embodiment, instead of directing the oxygen-bearing gas into the lungs, the oxygen-bearing gas can be directed into the upper airways, including, for example, using a catheter and, more particularly, a tracheal or coated catheter.

In one embodiment, an oxygen-bearing gas can be directed into the upper airways to treat or assist in the treatment of sleep apnea. Sleep apnea is a serious sleep disorder that occurs when a person's breathing is interrupted repeatedly during their sleep. People with untreated sleep apnea stop breathing repeatedly during their sleep, sometimes hundreds of times during the night. One type of sleep apnea can be referred to as obstructive sleep apnea (OSA). OSA is caused by a blockage of the airway, usually when the soft tissue in the rear of the throat collapses during sleep. Currently, sleep apnea can be treated by continuous positive airway pressure (CPAP) treatment in which a patient wears a mask over the nose and/or mouth. An air blower forces air through the upper airway. The air pressure is adjusted so that it is just enough to prevent the upper airway tissue from collapsing during sleep. The pressure is constant and continuous, and the flow rate is sometimes adjusted by bilevel positive airways pressure (Bi-PAP) machines, depending on need. CPAP can prevent airway closure while in use, but apnea episodes return when CPAP is stopped or it is used improperly. The use of the nasal mask and oral delivery of gas/oxygen/ambient air is cumbersome and inhibits the patient. In contrast, in accordance with the principles of the invention, the oxygen-bearing gas can be provided to the patient by way of a catheter, including a tracheal catheter. The oxygen-bearing gas can be provided to the patient based upon the breathing monitored by sensors in accordance with the invention. This includes sensors placed in the upper airway tissues that sense tissue movement or collapse. These sensors could communicate to the pump via wireless or hard wire. The sensors can detect the breathing cycles and based upon that information the oxygen flow and volume can be controlled. The oxygen-bearing gas can be provided continuously, intermittently, or pulsed as needed. Alternatively, as discussed above, the oxygen-bearing gas can be provided in a jet flow. Further, the portable respiration device can be programmed such that a continuous flow of oxygen-bearing gas is delivered and a jet boost is activated only if necessary. As a result, the oxygen can be tailored to the patient's needs.

The invention can be used to treat any kind of disease where alveolar ventilation and oxygen uptake are impaired. This includes chronic obstructive airway pulmonary diseases including lung emphysema, as well as restrictive diseases such as pulmonary fibrosis, sarcoidosis, pleural adhesions, chest-wall diseases, neuromuscular diseases, and phrenic nerve paralysis. Basically, whenever a patient has a problem breathing deeply enough, the invention can be helpful.

In contrast to the present invention, typical invasive ventilation is provided all the time, but a patient cannot exercise at all (walk, carry something, etc.). The patient has a tube in the throat and is fixed to a bed (usually in intensive care). Non-invasive ventilation with a mask is sometimes provided in order to help the patient's weak breathing muscles recover. For example, if the patient is ventilated overnight, the diaphragm and auxiliary muscles can rest, and the patient can perform better at daytime. However, whenever the patient would need help most (during exercise), the patient has to breathe on their own. With the minimally invasive or percutaneous ventilation and the synchronized jet from the system in accordance with the invention, support is given when needed (e.g., during exercise).

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes, which come within the meaning and range of equivalency of the claims, are to be embraced within their scope.

The invention claimed is:

1. An apparatus for supporting the respiration of a patient comprising:
   a gas pump operatively connected to an oxygen-bearing gas source,
   a control unit for activating the gas pump,
   a plurality of valves operatively connected to the control unit,
   sensors connected to the control unit for detecting spontaneous respiration of the patient including inhalation and exhalation, and
   a catheter adapted to be inserted into the respiratory system of the patient and fluidly connected to the gas pump;
   wherein a first subset of the valves are set to first predetermined positions and fluidly interconnect an output of the gas pump moving in a first stroke direction to the catheter to deliver a current flow during the patient inhalation, and a second subset of the valves are set to second predetermined positions and fluidly interconnects the output of the gas pump moving in a second, opposite direction to the catheter to deliver a countercurrent flow during patient exhalation;

wherein the catheter directs the current flow without turbulence to the lungs during the patient inhalation and attenuates flow by generated turbulence from the countercurrent flow during the patient exhalation.

2. The apparatus of claim 1 wherein the sensors include thermistors, pressure sensors, silicone wire strain gauges, respibands, respitrace, transthoracical electrical impedance measuring devices, flow sensors at the mouth or nose, or capnometers.

3. The apparatus of claim 1, wherein the sensors are connected to the control unit wirelessly.

4. The apparatus of claim 1, wherein the catheter is connected to a tracheal prosthesis within a trachea.

5. The apparatus of claim 4, wherein the tracheal prosthesis further comprises prongs or petals.

6. The apparatus of claim 4, wherein the tracheal prosthesis further comprises an antibacterial, a drug, a lubricious coating, hydrogel anesthetics, a treatment to prevent granulation tissue, or a treatment to prevent mucous formation coating.

7. The apparatus of claim 1, wherein the catheter further comprises a jet nozzle.

8. The apparatus of claim 7, wherein an exit port of the catheter is substantially centered in the trachea though the use of coils or bends in the catheter touching the walls of the trachea.

9. The apparatus of claim 7, wherein the catheter further comprises clips or a balloon.

10. The apparatus of claim 9, wherein the catheter has a single circumferential balloon or a plurality of balloons.

11. The apparatus of claim 9, wherein the clips are made of a resilient material.

12. The apparatus of claim 1, wherein the catheter comprises an inner lumen and an outer lumen.

13. The apparatus of claim 12, wherein the wall of the outer lumen comprises a plurality of ports.

14. The apparatus of claim 13, wherein the plurality of ports are substantially circular, hexagonal, oval, or slits.

15. The apparatus of claim 13, wherein the catheter further comprises a flow regulator adapted to regulate the flow of oxygen-bearing gas through the ports.

16. The apparatus of claim 15, wherein the flow regulator comprises a gliding sheath, shutters, louvers, or slats.

17. The apparatus of claim 1, further comprising a ventilator.

18. The apparatus of claim 1, wherein at least one nano device sensor is adapted to be implanted in the patient's body.

19. The apparatus of claim 1, wherein the oxygen-bearing gas from the oxygen-bearing gas source further comprises fragrances, aerosolized drugs, or water.

20. The apparatus of claim 19, wherein the oxygen-bearing gas is heated.

21. The apparatus of claim 1, wherein the control unit is programmed so that the respiratory device administers a continuous flow of oxygen-bearing gas from the oxygen-bearing gas source and a jet boost is activated only if necessary.

22. The apparatus of claim 1, wherein the sensors are disposed at different locations.

23. The apparatus of claim 22, wherein a signal response of a sensor is dampened relative to a signal response of an additional sensor, and wherein the signal response of the sensor and the signal response of the additional sensor are compared for correcting signal drift, transient signals and artifacts.

24. The apparatus of claim 1, wherein the gas pump, an oxygen-bearing gas source, and a control unit are housed together.

25. The apparatus of claim 1, wherein the countercurrent flow creates turbulence and is provided by an outer cannula of the catheter.

26. The apparatus of claim 1, wherein the catheter provides a variable direction flow.

27. The apparatus of claim 26, wherein the catheter provides flow towards the mouth.

28. The apparatus of claim 26, wherein the variable direction flow is provided by a gliding sheath.

29. The apparatus of claim 26, wherein the variable direction flow is vibratory flow.

30. The apparatus of claim 1, wherein the gas pump has a double-acting gas piston.

31. A method for supporting the respiration of a patient comprising the steps of:
    inserting a catheter into the respiratory system of the patient without hindering the patient's ability to speak,
    detecting spontaneous respiration of the patient with sensors, the respiration including an inhalation process and an exhalation process,
    identifying the end of the inhalation process,
    administering an additional amount of oxygen-bearing gas to the lungs without hindering the patient's ability to speak following the identified end of the inhalation process prior to commencing the exhalation process,
    administering an additional amount of oxygen-bearing gas to the lungs during the exhalation process to provide a countercurrent flow,
    wherein the catheter directs flow without turbulence toward the lungs during the inhalation process and attenuates flow by generated turbulence during the exhalation process.

32. The method of claim 31, wherein the oxygen-bearing gas is administered continuously, intermittently, or pulsed.

33. The method of claim 31, wherein the sensors include thermistors, pressure sensors, silicone wire strain gauges, respibands, respitrace, transthoracical electrical impedance measuring devices, flow sensors at the mouth or nose, or capnometers.

34. The method of claim 31, wherein the catheter is connected to a tracheal prosthesis.

35. The method of claim 34, wherein the tracheal prosthesis is secured in a trachea with prongs or petals.

36. The method of claim 34, further comprising supplying an antibacterial, a drug, a lubricious coating, hydrogel anesthetics, a treatment to prevent granulation tissue, or a treatment to prevent mucous formation to the patient by providing a tracheal prosthesis coated thereof.

37. The method of claim 31, wherein the catheter comprises an exit port, and wherein the exit port of the catheter is substantially centered in the patient's trachea.

38. The method of claim 37, wherein the exit port of the catheter is substantially centered in the trachea through the use of coils or bends in the catheter touching the walls of the trachea.

39. The method of claim 37, wherein the exit port of the catheter is substantially centered in the trachea though the use of clips or a balloon attached to the catheter.

40. The method of claim 39, wherein the catheter has a single circumferential balloon or a plurality of balloons.

41. The method of claim 39, wherein the clips are made of a resilient material.

42. The method of claim 31, wherein the catheter is introduced into the patient's respiratory system by way of the mouth or nose.

43. The method of claim 31, wherein the catheter comprises an outer lumen and an inner lumen, and wherein a wall of the outer lumen comprises a plurality of ports.

44. The method of claim 43, further comprising administering the oxygen-bearing gas through the inner lumen during inhalation and administering the oxygen-bearing gas through the outer lumen during exhalation.

45. The method of claim 31, further comprising applying vibratory flow to improve mucus clearance.

46. The method of claim 31, further comprising sensing high pressure in the trachea and shutting off the administration of oxygen-bearing gas.

47. The method of claim 31, wherein the oxygen-bearing gas comprises substantially pure oxygen, mixtures of oxygen and nitrogen, mixtures of oxygen and inert gases, ambient air, or various combinations thereof.

48. The method of claim 47, wherein the oxygen-bearing gas further comprises fragrances, aerosolized drugs, or water.

49. The method of claim 47, wherein the oxygen-bearing gas is heated.

50. The method of claim 31, wherein the control unit is programmed so that the oxygen-bearing gas delivery device administers a continuous flow of oxygen-bearing gas and a jet boost is activated only if necessary.

51. The method of claim 31, administering the oxygen-bearing gas in a variable direction.

52. The method of claim 31, administering the oxygen-bearing gas toward the mouth during exhalation.

53. The method of claim 31, wherein the amount of carbon dioxide exhaled is increased by between 5% and 30%.

54. The method of claim 31, wherein the amount of carbon dioxide exhaled is increased by between 20% and 30%.

* * * * *